United States Patent [19]

Olander et al.

[11] Patent Number: 5,036,003

[45] Date of Patent: Jul. 30, 1991

[54] ANTIBODIES TO VPF

[75] Inventors: Jitka V. Olander, University City; Daniel T. Connolly, Manchester; Steven P. Adams, St. Charles; Joseph Feder, University City, all of Mo.

[73] Assignee: Monsanto Company, St. Louis, Mo.

[21] Appl. No.: 240,780

[22] Filed: Sep. 2, 1988

Related U.S. Application Data

[63] Continuation-in-part of Ser. No. 87,739, Aug. 21, 1987, Pat. No. 5,008,196.

[51] Int. Cl.$^5$ .................. C12P 21/00; C12P 21/08
[52] U.S. Cl. ................. 435/70.1; 435/70.2; 435/70.21; 435/172.2; 435/240.2; 435/240.27; 530/387
[58] Field of Search ............. 424/88; 435/7, 68, 70, 435/70.1, 70.2, 70.21, 70.4, 172.2, 240.26, 240.27; 935/106; 436/547, 548; 530/387, 807, 828

[56] References Cited

U.S. PATENT DOCUMENTS

| | | | |
|---|---|---|---|
| 4,456,550 | 6/1984 | Dvorak et al. | 424/95 |
| 4,652,629 | 3/1987 | Patrick et al. | 530/403 |
| 4,795,803 | 1/1989 | Lindberg et al. | 530/403 |
| 4,818,527 | 4/1989 | Thornton et al. | 530/403 |

OTHER PUBLICATIONS

Stites et al., Basic & Clinical Immunology, 1984, pp. 22-25.
Senger et al., Canc. Res., 46:5629-5632, 1986, "A Highly Conserved Vascular Permeability Factor Secretely by a Variety of Human & Rodent Tumor Cell Lines".
Kohler et al., Nature, 256:495-497, 1975, "Continuous Cultures of Fused Cells Secreting Antibody of Predetermined Specificity".
Senger et al., Science 219, 983-985 (1983).
Folkman and Klagsbrun, Science, 235, 442-447 (1987).
Dvorak et al., J. Immunol., 122(1), 166-174 (1979).
Dvorak, N. Engl. J. Med. 315, 1650-1659 (1986).
Kadish et al., Tissue & Cell 11, 99 (1979).
Dvorak et al., J. Natl. Cancer Inst. 62, 1459-1472 (1979).
Lobb et al., Int. J. Cancer 36, 473-478 (1985).

Primary Examiner—Elizabeth C. Weimar
Assistant Examiner—Gail Poulos
Attorney, Agent, or Firm—Scott J. Meyer; James W. Williams, Jr.

[57] ABSTRACT

A method of producing antibodies against vascular permeability factor (VPF) is disclosed which comprises immunizing a host animal with a peptide having an amino acid sequence as follows:

```
1               5                10              15
AlaProMetAlaGluGlyGluGlnLysProArgGluValValLys 16              20               25              30
PheMetAspValTyrLysArgSerTyrCysArgProIleGluMet 31          35
LeuValAspIlePheGln
``` or a fragment of said peptide containing an antigenic determinant of VPF.

4 Claims, 1 Drawing Sheet ary of 35,000-43,000 daltons.

ANTIBODIES TO VPF

CROSS-REFERENCE TO RELATED APPLICATION

This is a continuation-in-part of copending application Ser. No. 87,739, filed Aug. 21, 1987, now U.S. Pat. No. 5,008,196.

BACKGROUND OF THE INVENTION

This invention relates to antibodies against vascular permeability factor and, more particularly, to a method of producing said antibodies by immunization with synthetic peptide fragments of a vascular permeability factor.

Vascular permeability factors (VPFs) are proteins originally obtained from a variety of tumors which cause a rapid and reversible increase in blood vessel permeability when nanogram amounts are injected under the skin of a warm blooded mammal. VPF activity has been found in tumor ascites fluids from guinea pigs, hamsters and mice and is secreted by these tumors and a variety of tumor cell lines in vitro according to Senger et al., *Science* 219, 983–985 (1983).

In U.S. Pat. No. 4,456,550, a purified VPF is described which has the following characteristics:

(a) in an aqueous solution (0.01M $Na_3PO_4$, pH 7) whose concentration of NaCl is varied linearly, VPF is eluted from a heparin-Sepharose chromatography column in a peak centered at 0.4 NaCl;

(b) in an aqueous solution of $Na_3PO_4$ (pH 7.0) whose concentration is varied linearly, VPF is eluted from a hydroxylapatite column in a peak centered at 0.25M $Na_3PO_4$; and (c) when subjected to SDS gel electrophoresis in a 7.5% polyacrylamide slab gel (0.375M tris-HCl, pH 8.8, 0.1% SDS) at 35 milliamps and 4° C., VPF is localized to a region corresponding to a molecular weight between 34,000 and 45,000 daltons.

The VPF was purified about 1800 fold from serum-free conditioned medium of guinea pig tumor cell culture or 10,000 fold from ascites fluid by a series of steps consisting of:

(a) affinity chromatography with a column of heparin-Sepharose;
(b) chromatography with a column of hydroxylapaptite; and
(c) sodium dodecylsulfate/polyacrylamide gel electrophoresis.

As little as 200 ng ($5 \times 10^{-12}$ moles) of this purified VPF increased the vascular permeability equivalent to 1.25 $\mu g$ ($4 \times 10^{-9}$ moles) of histamine. Histamine is a standard permeability mediator described by Miles and Miles, *J. Physiol.* 118, 228–257 (1952). The VPF is said to have therapeutic value insofar as it enables blood nutrients to reach tissue with increased need for nutrients, as in wound healing. Antibody against the VPF is said to have therapeutic value insofar as it blocks a tumor's ability to increase vessel permeability and thereby to obtain nutrients from increased vessel leakage.

According to Folkman and Klagsbrun, *Science* 235, 442–447 (1987), VPF causes leakage of proteins, including fibrinogen, from blood vessels, thereby initiating the formation of a fibrin gel which, in turn, may play a role in angiogenesis. See also Dvorak et al., *J. Immunol.* 122(1), 166–174 (1979); Dvorak, *N. Engl. J. Med.* 315, 1650–1659 (1986); Kadish et al., *Tissue Cell* 11, 99, (1979); Dvorak et al., *J. Natl. Cancer Inst.* 62, 1459–1472 (1979); and Senger et al., *Cancer Res.* 46, 5629–5632 (1986).

Lobb et al., *Int. J. Cancer* 36, 473–478 (1985), partially purified a VPF from a human adenocarcinoma cell line HT-29 having a molecular weight of 45,000. This VPF, however, does not bind to immobilized heparin as does the VPF derived from guinea pig tumor cell material by Senger and Dvorak.

The copending application Ser. No. 87,739, filed Aug. 31, 1987, a method of stimulating endothelial cell growth is provided which comprises subjecting said cells to a growth stimulating amount of a highly purified vascular permeability factor (VPF). The disclosure of said copending application is incorporated herein by reference. The highly purified VPF has the following characteristics:

(a) it has a $M_r$ about 34,000–40,000 as determined by sodium dodecylsulfate polyacrylamide gel electrophosphoresis (SDS/PAGE);
(b) it is a disulfide-linked protein dimer;
(c) it has a N-terminal amino acid sequence as follows:

```
1               5                  10                 15
AlaProMetAlaGluGlyGluGlnLysProArgGluValValLys 16              20                 25                 30
PheMetAspValTyrLysArgSerTyrCysArgProIleGluMet 31              35
LeuValAspIlePheGln; and
```

(d) it exhibits substantial mitogenic activity to endothelial cells in culture.

The foregoing highly purified VPF was isolated from serum-free conditioned culture medium of guinea pig tumor cells in a series of steps comprising:

(a) affinity chromatography of said conditioned culture medium with a column of heparin-Sepharose CL-6B;
(b) cation exchange chromatography of the VPF active fractions from said affinity chromatography with a TSK SP-5-PW column;
(c) high performance liquid chromatography (HPLC) of the VPF active fractions from said cation exchange chromatography with a Vydac $C_4$ reversed phase HPLC column; and
(d) HPLC of the VPF active fractions from said $C_4$ HPLC with a Vydac $C_{18}$ reversed phase HPLC column.

The mitogenic activity of the VPF to endothelial cells in culture was demonstrated by an increase in cell number and in $^3H$-thymidine incorporation into deoxyribonucleic acid (DNA) relative to control cultures after several days following addition of the VPF to cultures of bovine aortic endothelial (BAE) cells. In these tests, half maximal stimulation of growth was observed at $5 \times 10^{-11}$ M VPF, and half maximal stimulation of $^3H$-thymidine incorporation into DNA was observed at $2.5 \times 10^{-12}$ M VPF. The in vitro mitogenic response, as measured by the $^3H$-thymidine incorporation, was thus about 400 times more sensitive to VPF concentration than the in vivo permeability response since the dose required for a measurable increase in permeability is $1 \times 10^{-9}$ M. The mitogenic activity of VPF to endothelial cells in culture thereby is distinct and separate from its vascular permeability activity and was surprising and unexpected since the VPF did not stimulate or only slightly stimulated $^3$H-thymidine incorporation or cell growth of other cell types such as 3T3 mouse fibroblasts and mouse smooth muscle cells.

BRIEF DESCRIPTION OF THE INVENTION

In accordance with the present invention an improved method of producing antibodies against vascular permeability factor (VPF) is provided. The method comprises immunization of a host animal with synthetic peptides comprising the N-terminal 36 amino acid sequence of VPF as defined in copending application Ser. No. 87,739, filed Aug. 21, 1987, or a fragment thereof containing an antigenic determinant of VPF. The VPF N-terminal synthetic peptide has the following sequence:

VPF(1-36)

```
 1             5               10              15
AlaProMetAlaGluGlyGluGlnLysProArgGluValValLys 16            20              25              30
PheMetAspValTyrLysArgSerTyrCysArgProIleGluMet 31            35
LeuValAspIlePheGln.
```

In the above amino acid sequence, conventional three letter abbreviations are used to designate the individual amino acids.

Preferred fragments an antigenic N-terminal sequence containing an antigenic determinant of VPF are VPF(1-15) and VPF(1-21).

Both polyclonal and monoclonal antibodies against VPF can be produced by using the aforesaid peptides as unique immunogens in standard immunization protocols. Various of the antibodies thus produced were found to be effective in blocking the permeability-enhancing activity of VPF as determined by the Miles assay. These results were surprising and unexpected since it was not previously known that these peptides, which are only small fragments of the 34,000-40,000 molecular weight VPF, would even be immunogenic in the first place. Moreover, it was not predictable that antibodies which were found to bind a given protein would also block the activity of said protein.

BRIEF DESCRIPTION OF THE DRAWING

FIG. 1 is a graphical representation which shows a standard curve in which ng/ml VPF are plotted against absorption ($A_{490}$) in a quantitative ELISA for guinea pig VPF.

DETAILED DESCRIPTION OF THE INVENTION

The synthetic peptides used as immunogens in this invention can be made by appropriate adaptation of conventional methods for peptide synthesis. Thus, the peptide chain can be prepared by a series of coupling reactions in which the constituent amino acids are added to the growing peptide chain in the desired sequence. The use of various N-protecting groups, e.g., the carbobenzyloxy group or the t-butyloxy-carbonyl group (BOC), various coupling reagents, e.g., dicyclohexylcarbodiimide or carbonyldimidazole, various active esters, e.g., esters of N-hydroxy-pthalimide or N-hydroxy-succinimide, and various cleavage reagents, e.g., trifluoroacetic acid, HCL in dioxane, boron tris-(trifluoroacetate) and cyanogen bromide, and reaction in solution with isolation and purification of intermediates is well-known classical peptide methodology.

Preferably, the peptide immunogen used in this invention is prepared by the well-known Merrifield solid support method. See Merrifield, J. Amer. Chem. Soc. 85, 2149-54 (1963) and Science 150, 178-85 (1965). This procedure, though using many of the same chemical reactions and blocking groups of classical peptide synthesis, provides a growing peptide chain anchored by its carboxyl terminus to a solid support, usually cross-linked polystyrene or styrene-divinylbenzene copolymer. This method conveniently simplifies the number of procedural manipulations since removal of the excess reagents at each step is effected simply by washing of the polymer.

The general reaction sequence for typical Merrifield peptide synthesis can be illustrated by the following sequence of steps:

I. A chloromethylation step to provide a reactive group for attachment of the peptide to the polystyrene resin;

II. An esterification step involving reaction with triethylammonium salt of the first protected amino acid using a t-BOC protecting group;

III. A peptide forming step with dicyclohexylcarbodiimide coupling reagent;

IV. Cleavage of t-BOC such as by treatment, for example, with 25% trifluoracetic acid in methylene chloride and liberation of N-terminal amine by excess of triethylamine, thereby enabling it to react with the activated carboxyl of the next protected amino acid; and V. Cleavage of the completed peptide from the polystyrene resin such as by treatment, for example, with anhydrous HF in anisole.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in Advances in Enzymology 32, pp. 221-296, F. F. Nold, Ed., Interscience Publishers, New York, 1969; and Erickson and Merrifield, The Proteins, vol. 2, p. 255 et seq. (ed. Neurath and Hill), Academic Press, New York, 1976.

Following preparation of the synthetic peptides, the polyclonal antibodies against the peptide antigens can be produced in a manner generally similar to known methods for producing antibodies such as by immunizing a suitable animal host, for example, rabbits, guinea pigs and the like animals, by repeated injections of small amounts of the peptide coupled to a carrier protein and combined with an adjuvant such as, for example, Freund's complete adjuvant. The antibodies produced in the animal are then recovered from the blood serum after a suitable immunization period. The presence of antibodies in the sera can be determined by standard immunologic techniques of double diffusion gel precipitation in agar gel, electrophoresis, immunoelectrophoresis, enzyme immunoassays such as ELISA and the like methodology.

The monoclonal antibody production can be carried out by conventional procedure such as described, for example, by Köhler and Milstein, Nature 256, 495-497 (1975); Eur. J. Immunol. 6, 511-519 (1976). According to this method, tissue-culture adapted mouse myeloma cells are fused to spleen cells from immunized mice to obtain the hybrid cells that produce large amount of a single antibody molecule. In this procedure, the aforesaid synthetic VPF peptides bound to a carrier protein, preferably bovine serum albumin or thyroglobulin, are used as the immunogens. The carrier protein, which can be natural protein molecules, synthetic peptides, or equivalent polymeric particles, is used to enhance immunogenicity of the peptide antigen. The albumins (e.g., human, bovine, or rabbit), synthetic peptides (e.g., polylysine) and polymers (e.g., polyvinylpyrrolidone) are commonly used as carriers for antibody production. The bovine serum albumin-derivatized peptide can be prepared by glutaraldehyde coupling and other conventional general procedure such as described, for example, Lieberman et al., *Rec. Prog. Hor. Res.* 15, 165 (1959).

A preferred mouse myeloma cell line for use in making these antibodies is the Sp2/0-Ag14 cell line. This is a well-known cell line of BALB/c origin defined by Schulman, Wilde and Köhler, *Nature* 276, 269-270 (1978), the disclosure of which is incorporated herein by reference. These cells, which do not synthesize Ig chains, can be obtained from the Basel Institute for Immunology and are readily available to the public from the American Type Culture Collection, Rockville, Md., under accession number ATCC CRL-1581. A preferred method of carrying out the fusion of the myeloma cells and the spleen cells is by the conventional general procedure described by Galfre et al., *Nature* 266, 550-552 (1977). This method employs polyethylene glycol (PEG) as the fusing agent for the cells growing as monolayers, followed by selection in HAT medium (hypoxanthine, aminopterin and thymidine) as described by Littlefield, *Science* 145, 709-710 (1964).

Isolation and purification of the monoclonal antibodies from the cell culture medium can be carried out by known methods such as, for example, ammonium sulfate precipitation, dialysis, affinity chromatography, ion exchange chromatography, gel filtration and the like methods. See also U.S. Pat. No. 4,533,496 for isolation of monoclonal antibodies by use of polyelectrolyte copolymers.

Further background information on suitable methodology for producing monoclonal antibodies can be had by reference to texts in the field, for example, Goding, "Monoclonal Antibodies: Principles and Practice," Academic Press, N.Y., 1983.

It will be appreciated that not all hybridomas prepared as described herein will have optimum antibody activity. As is customary in this field, radioimmunoassay and enzyme immunoassay procedures can be readily used to screen the population of hybridomas for individual clones which secrete the optimum specificity. The radioimmunoassay is based upon the competition between radiolabeled and unlabeled antigen for a given amount of antibody which can be determined by conventional general procedure as described, for example, by Yalow et al., *J. Clin. Invest.* 39, 1157 (1960). In the enzyme immunoassay such as ELISA, the revealing agent is conjugated with an enzyme instead of $^{125}I$. After washing away any unbound material, the bound enzyme is revealed by addition of a substrate which undergoes a color change. See, e.g., Engvall and Perlmann, *Immunochemistry* 8, 871-874 (1971); *J. Immunol.* 109, 129-135 (1972).

The following examples will further illustrate the invention although it will be understood that the invention is not limited to these specific examples.

EXAMPLE 1

Peptide Synthesis. VPF(1-21) containing the N-terminal 21 amino acid sequence of VPF, as set forth below, was synthesized by the Merrifield solid support method on an Applied Biosystems Model 430A Peptide Synthesizer using phenylacetamideomethyl resin. t-Butyloxycarbonyl amino acids were were converted to symmetrical anhydrides using dicyclohexylcarbodiimide, except for arginine and glutamine which were coupled as hydroxybenzotriazole esters. The peptide was cleaved from the resin and side-chain blocking groups removed with liquid hydrogen fluoride/anisole (9:1, v/v) for 1 hour at 0° C. Free peptide was extracted from the resin with 30% acetic acid, filtered, and lyophilized. Purification was performed by preparative high performance liquid chromatography (HPLC) on a μBondapak $C_{18}$ column (19×250 mm) using a linear gradient of 5-45% acetonitrile in 0.05% trifluoroacetic acid over 30 minutes with a flow rate of 9 ml/minute. The major peak eluted at 28% acetonitrile and was isolated and lyophilized. Analytical HPLC using a Vydac $C_{18}$ column (The Separations Group, Hesperia, Calif.) revealed greater than 95% purify of the product. Peptide composition was confirmed by amino acid analysis.

VPF(1-21)

```
1              5             10             15
AlaProMetAlaGluGlyGluGlnLysProArgGluValValLys 16           21
PheMetAspValTyrLys
```

EXAMPLE 2

Polyclonal Rabbit Antibodies to VPF(1-21) (FOO3)

3.7 mg of VPF(1-21), as prepared in Example 1, above, were conjugated to 7.4 mg bovine thyrogluobulin, using glutaraldehyde followed by dialysis. The conjugate was stored lyophilized in aliquots at −20° C. Rabbit F003 was given the primary immunization with 100 μg conjugate in complete Fruend's adjuvant in a total of 1 ml injected subcutaneously in multiple sites on the back. Boosts of 100 μg conjugate in incomplete Freund's adjuvant in 2 ml were injected in the same manner four and twelve weeks later. The rabbit was bled 4 weeks and 4 weeks after the first boost and every two weeks after the second boost during a period of four months.

RESULTS

When anti-VPF(1-21) serum, as prepared above, was mixed with VPF before testing in the Miles assay, [Miles and Miles, *J. Physiol.* 118, 228-257 (1952)], the permeability-enhancing activity of VPF was completely blocked. The serum when diluted 1:32 still blocked activity. Control serum did not block activity.

When purified VPF as described in copending application Ser. No. 87,739 was treated with protein A-Sepharose ® to which anti-VPF(1-21) was adsorbed, essentially all of the permeability-enhancing activity was removed from the sample as determined by the Miles assay. IgG from non-immunized rabbits was without effect. Similarly, the growth-promoting activity in VPF preparations was removed with anti-VPF(1-21) IgG but not with control IgG. Fetal bovine aortic endothelial cells (BAE) were plated into 12-well dishes (4 cm²) at a density of 16,000 cells/well. For immunoadsorbtion, 200 μl of protein A-Sepharose was incubated for 1 hour at room temperature with 200 μl of either pre-immune serum or anti-VPF(1-21) serum. The protein A-Sepharose was washed 3 times with 1 ml phosphate buffered saline (PBS) and incubated with 10 μg VPF at 4° C. for 24 hours. The VPF samples were removed and added to the cultures on days 1 and 3 after diluting 1:500. Cells were counted on day 6. The results are shown in Table I, below.

TABLE I

| Effect of Anti-VPF (1-21) Immunoadsorbtion on VPF-Growth Promoting Activity | |
|---|---|
| Treatment | Cells/Well (± S.D.) |
| None | 120,000 ± 11,000 |
| Pre-Immune IgG + VPF | 194,000 ± 16,000 |
| Anti-VPF (1-21) IgG + VPF | 138,000 ± 13,000 |

S.D. = Standard deviation

EXAMPLE 3

Hybridomas were prepared from immune murine spleen cells and Sp2/0-Ag14 myeloma cells using standard hybridoma fusion and subcloning technique as published by Goding, supra. VPF(1-21) conjugated with bovine thyroglobulin carrier was used as the immunogen. The mouse was initially immunized with 50 μg of the antigen emulsified in complete Freund's adjuvant followed by boosts with 50 μg of the antigen in incomplete Freund's adjuvant at 4 weeks and 50 μg of the antigen in phosphate buffered saline by tail vein injection at 19 weeks, 3 days prior to spleen removal. The hybridomas and subclones were screened by ELISA in which monoclonal antibodies were captured by biotinylated VPF(1-21) peptide bound to avidin coated microtiter plates. The monoclonal antibodies were detected by horseradish peroxidase conjugated goat-anti-mouse Ig serum with the enzyme acting on its substrate, hydrogen peroxide coupled to the chromophore, o-phenylenediamine.

Seven hybridomas thus produced were stable and produced monoclonal antibodies reactive with the VPF(1-21) peptide as well as with the complete purified VPF protein. These monoclonal antibodies, however, did not block VPF activity in the Miles assay.

Monoclonal antibodies from two of the foregoing hybridomas, designated VPF 17B4.5 and VPF 17C4.6, were purified from the cell culture media and coupled to cyanogen bromide activated Sepharose ®. The resulting immunoadsorbents removed VPF activity from guinea pig Line 10 tumor conditioned media; the activity was recovered by elution with buffer at pH 4.0. Thus, these monoclonal antibodies are useful as immunoadsorbents for VPF isolation and an captive antibodies in a quantitative ELISA for VPF.

EXAMPLE 4

Monoclonal antibodies as prepared in Example 3 were used in a quantitative ELISA for guinea pig VPF (gVPF) as follows:

Microtiter wells were coated with 50 μl of 10 μg/ml monoclonal antibody to VPF(1-21), 17C4.6, in 0.1M NaHCO₃ buffer, pH 9.8, for 3 hours and then blocked with 10% powdered milk in the same buffer. This was followed by known dilutions of gVPF and samples with gVPF (50 μl/well) which were allowed to bind overnight at room temperature. The bound gVPF was reacted with 1/500 dilution of IgG fraction of rabbit polyclonal anti-gVPF serum (F001) for 4 hrs followed by 1/2000 dilution of Bio-Rad's horseradish peroxidase (HRP) conjugated goat-anti-rabbit serum for 2 hrs. The amount of HRP bound was detected with the hydrogen peroxide substrate coupled with o-phenylenediamine, reacted at pH 5.0. All dilutions were done in 1% powdered milk in PBS+0.05% Tween ® 20 except for the initial coating and the final substrate. Between each binding step the wells were washed 3× with 200 μl 0.15M NaCl, 0-05% Tween ® 20.

FIG. 1 shows the resulting standard curve in which ng/ml gVPF are plotted against absorption (A₄₉₀).

EXAMPLE 5

Another synthetic peptide fragment of VPF was prepared by solid phase peptide synthesis as in Example 1 as follows:

VPF(1-15)

```
1         5         10        15
AlaProMetAlaGluGlyGluGlnLysProArgGluValValLys
```

The peptide VPF(1-15) was coupled to bovine thyroglobulin carrier protein with glutaraldehyde.

Rabbits were immunized with the equivalent of 100 μg peptide per rabbit per immunization. The primary immunization was done in complete Freund's adjuvant followed by two boosts, a month apart, in incomplete Freund's adjuvant. The rabbits were bled two weeks after the second boost and their antisera analyzed. The peptide was thereby used to immunize two rabbits. Antisera from the immunized rabbits blocked VPF activity in the Miles Assay at dilutions of 1:5 to 1:10.

Substantially similar results as described in Examples 2 to 5, above, are obtained when VPF(1-36) is used as the immunogen instead of VPF(1-15) and VPF(1-21) in these examples.

A search of the CAS database, CASSEQ, revealed no sequence homology between VPF(1-36) and peptide segments of other proteins.

Various other examples will be apparent to the person skilled in the art after reading the present disclosure without departing from the spirit and scope of the invention. It is intended that all such other examples be included within the scope of the appended claims.

What is claimed is:

1. A method of producing antibodies which block the permeability-enhancing and growth-promoting activities of vascular permeability factor (VPF) comprising immunizing an animal host with a synthetic peptide having an amino acid sequence as follows:

```
1         5         10        15
AlaProMetAlaGluGlyGluGlnLysProArgGluValValLys.
```

2. A method of producing antibodies which block the permeability-enhancing and growth-promoting activities of vascular permeability factor (VPF) comprising immunizing an animal host with a synthetic peptide having an amino acid sequence as follows:

```
1         5         10        15
AlaProMetAlaGluGlyGluGlnLysProArgGluValValLys
16        21
PheMetAspValTyrLys.
```

3. A method of producing a monoclonal antibody which blocks the permeability-enhancing and growth-promoting activities of vascular permeability factor (VPF) comprising:

(a) immunizing a mouse with a synthetic peptide having the amino acid sequence as follows:

```
   1           5              10                 15
   AlaProMetAlaGluGlyGluGlnLysProArgGluValValLys
``` and in which the immunizing peptide is coupled to bovine serum albumin or thyroglobulin carrier protein, (b) harvesting spleen cells from said mouse, and (c) fusing spleen cells with mouse myeloma cells to obtain a monoclonal antibody capable of blocking VPF activity.

4. A method of producing a monoclonal antibody which blocks the permeability-enhancing and growth-promoting activities of vascular permeability factor (VPF) comprising:

(a) immunizing a mouse with a synthetic peptide having the amino acid sequence as follows:

```
   1           5              10                 15
   AlaProMetAlaGluGlyGluGlnLysProArgGluValValLys
   16          21
   PheMetAspValTyrLys,
``` and in which the immunizing peptide is coupled to bovine serum albumin or thyroglobulin carrier protein, (b) harvesting spleen cells from said mouse, and (c) fusing spleen cells with mouse myeloma cells to obtain a monoclonal antibody capable of blocking VPF activity.

* * * * *